US012758613B2

(12) United States Patent
Choi et al.

(10) Patent No.: US 12,758,613 B2
(45) Date of Patent: Oct. 13, 2026

(54) METHOD FOR REDUCING INSULIN RESISTANCE OR TOTAL BLOOD CHOLESTEROL LEVELS BY ADMINISTERING BONE MORPHONGENETIC PROTEIN 10

(71) Applicant: GIL MEDICAL CENTER, Incheon (KR)

(72) Inventors: Cheol Soo Choi, Incheon (KR); Jee-Hyun Um, Busan (KR); Shi-Young Park, Incheon (KR)

(73) Assignee: GIL MEDICAL CENTER, Incheon (KR)

( * ) Notice: Subject to any disclaimer, the term of this patent is extended or adjusted under 35 U.S.C. 154(b) by 914 days.

(21) Appl. No.: 18/072,750

(22) Filed: Dec. 1, 2022

(65) Prior Publication Data

US 2023/0124505 A1 Apr. 20, 2023

Related U.S. Application Data

(63) Continuation of application No. PCT/KR2021/012000, filed on Sep. 6, 2021.

(30) Foreign Application Priority Data

Oct. 30, 2020 (KR) ........................ 10-2020-0142708

(51) Int. Cl.

| | |
|---|---|
| ***A61K 38/19*** | (2006.01) |
| ***A23L 33/00*** | (2016.01) |
| ***A23L 33/17*** | (2016.01) |
| ***A61K 38/18*** | (2006.01) |
| ***A61P 3/04*** | (2006.01) |
| ***A61P 3/06*** | (2006.01) |
| ***A61P 3/10*** | (2006.01) |

(52) U.S. Cl.
CPC .......... *A61K 38/1875* (2013.01); *A23L 33/17* (2016.08); *A23L 33/30* (2016.08); *A61P 3/04* (2018.01); *A61P 3/06* (2018.01); *A61P 3/10* (2018.01)

(58) Field of Classification Search
None
See application file for complete search history.

(56) References Cited

U.S. PATENT DOCUMENTS

2006/0239951 A1 10/2006 Valentin et al.

FOREIGN PATENT DOCUMENTS

| | | | |
|---|---|---|---|
| CN | 105136781 | A | 12/2015 |
| JP | 2019-210290 | A | 12/2019 |
| KR | 10-2016-0101786 | A | 8/2016 |
| WO | 2005-113590 | A2 | 12/2005 |
| WO | 2007-099345 | A1 | 9/2007 |
| WO | 2009-084739 | A1 | 7/2009 |

OTHER PUBLICATIONS

Wang et al. (J. Cell Mol Med. 28: e18324, 2024).*
Marlatt et al. (Curr. Obes. Rep. 6: 389-396, 2017).*
Zuriaga et al. ((2017) Humans and Mice Display Opposing Patterns of “Browning” Gene Expression in Visceral and Subcutaneous White Adipose Tissue Depots. Front. Cardiovasc. Med. 4: 27).*
Zhang et al. (Factors Associated with White Fat Browning: New Regulators of Lipid Metabolism. Int. J. Mol. Sci. 2022, 23, 7641).*
Schulz, T. J. et al., “Emerging role of bone morphogenetic proteins in adipogenesis and energy metabolism”, Cytokine & Growth Factor Reviews, 2009, vol. 20, pp. 523-531.
Tseng, Y. H. et al., “New role of bone morphogenetic protein 7 in brown adipogenesis and energy expenditure”, Aug. 21, 2008, vol. 454, pp. 1000-1004.
Koncarevic, A. et al., “A Novel Therapeutic Approach to Treating Obesity through Modulation of TGFB Signaling”, Endocrinology, 2012, vol. 153, pp. 3133-3146.

* cited by examiner

*Primary Examiner* — Christine J Saoud
(74) *Attorney, Agent, or Firm* — Revolution IP, PLLC

(57) ABSTRACT

Provided are methods of reducing insulin resistance and reducing total blood cholesterol levels in a subject in need thereof. Each method comprises parenterally administering a pharmaceutical composition comprising bone morphogenetic protein 10 (BMP10) as an active ingredient to the subject. In a high-fat-diet-induced obese animal model, parenteral administration of BMP10 significantly lowered fasting blood glucose and lowered insulin secretion relative to a control, confirming an improvement in insulin resistance, and significantly reduced total blood cholesterol levels relative to the control. The methods are useful for reducing insulin resistance and for reducing total blood cholesterol levels in the subject.

4 Claims, 7 Drawing Sheets

Control BMP10

Day 4

Day 8

[Fig. 4]
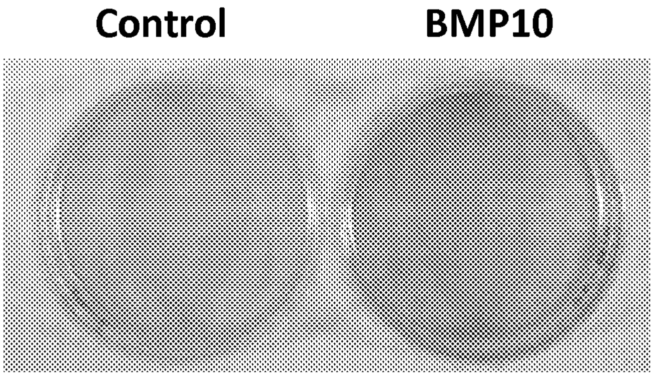

[Fig. 5]
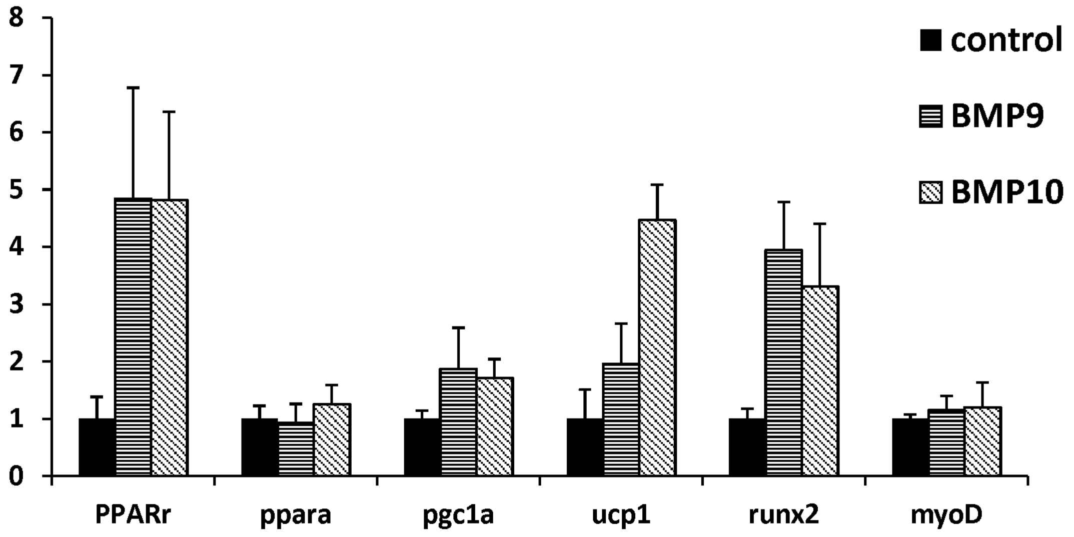

[Fig. 6]
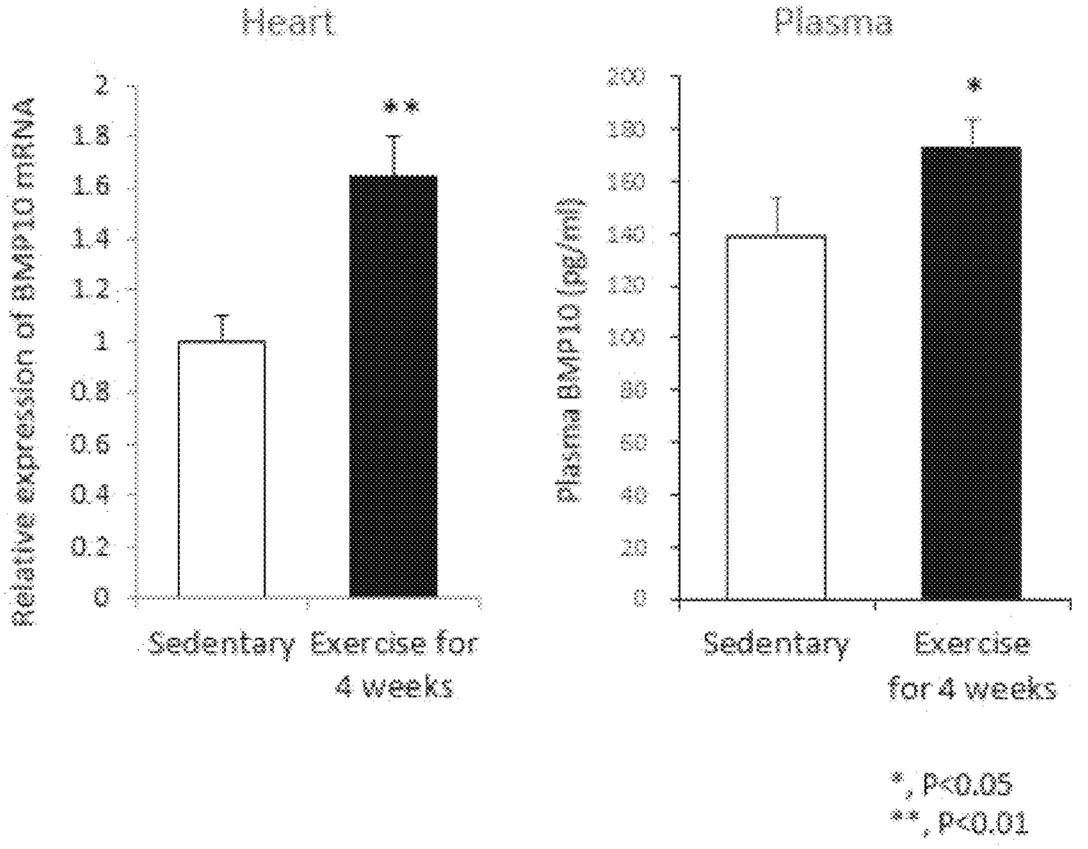

[Fig. 7]
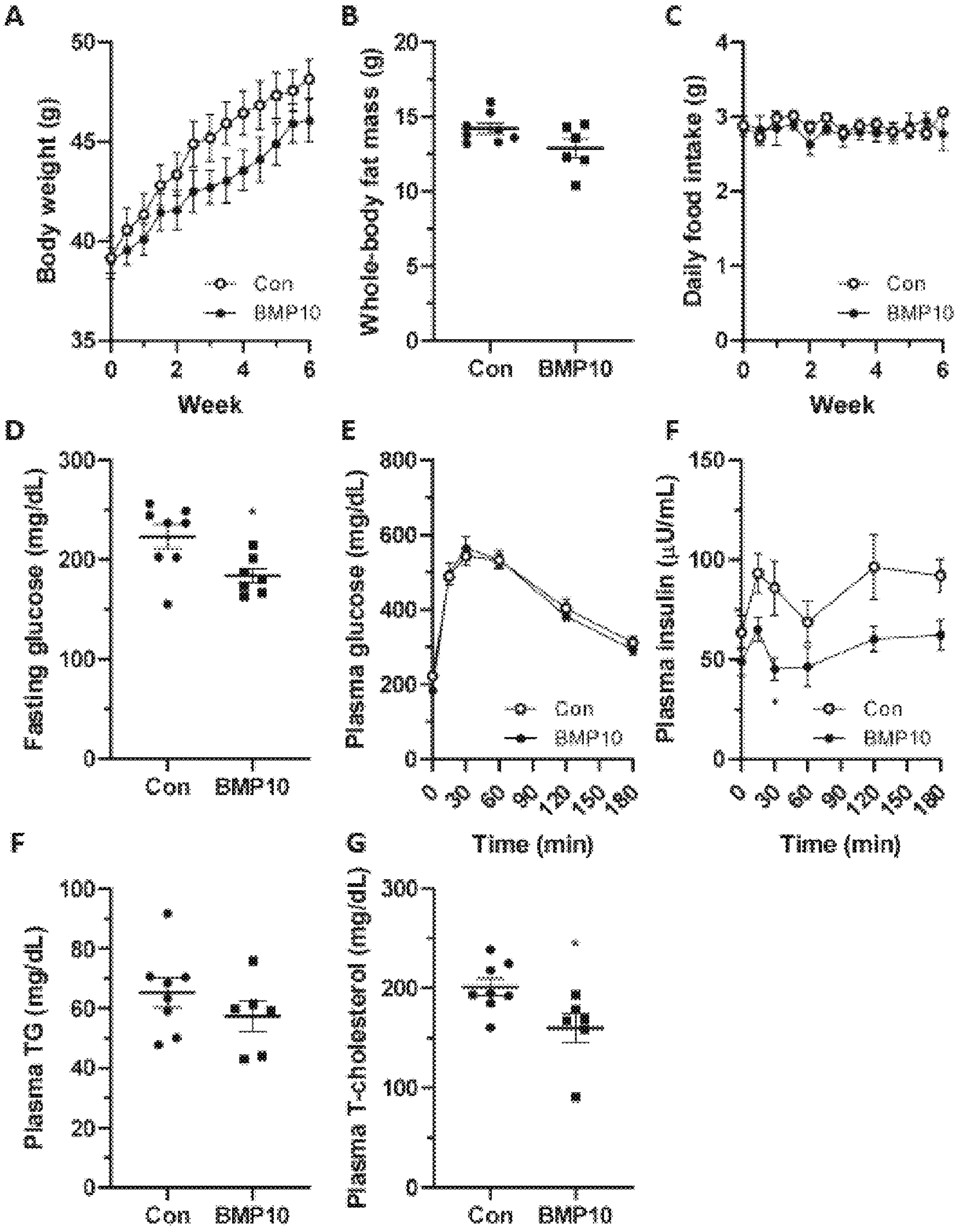

METHOD FOR REDUCING INSULIN RESISTANCE OR TOTAL BLOOD CHOLESTEROL LEVELS BY ADMINISTERING BONE MORPHONGENETIC PROTEIN 10

TECHNICAL FIELD

The present disclosure relates to a composition for preventing or treating metabolic diseases containing bone morphogenetic protein 10 as an active ingredient.

BACKGROUND ART

Obesity is caused by an imbalance between energy intake and consumption, and excess energy is converted into fatty acid and stored in the body. Under obese condition, the secretion of excess free fatty acids and cytokines from enlarged adipocytes induce insulin resistance and inflammatory responses, which is a direct cause of the onset of chronic diseases such as metabolic syndrome, diabetes, cardiovascular disease, and cancer.

In order to treat obesity, improvement of eating habits through exercise and diet therapy, drug therapy, and treatment through surgery have been introduced, and with development of anti-obesity drugs that suppress double obesity, more than 100 therapeutic drugs are sold or in development in the United States, and the market size is expected to grow.

Currently, drugs for treating obesity may be divided into drugs that affect appetite by acting on the central nervous system and drugs that inhibit absorption by acting on the gastrointestinal tract. As the drugs acting on the central nervous system, drugs such as fenfluramine and dexfenfluramine that inhibit the serotonin (5HT) nervous system according to their respective mechanisms, drugs such as ephedrine and caffeine through the noradrenergic nervous system, and recently, drugs such as sibutramine that act serotonin and the noradrenergic nervous system simultaneously to inhibit obesity, are commercially available.

However, among drugs that have been used in the past, fenfluramine has recently been banned because of side effects such as primary pulmonary hypertension or heart valve lesions. Sibutramine has side effects that increase blood pressure, and Orlistat has been reported to have side effects such as digestive disorders, fatty stools, bowel incontinence, and obstruction of absorption of fat-soluble vitamins. In addition, other chemically synthesized drugs also have problems such as blood pressure reduction or lactic acidemia, so that they cannot be used for patients with heart failure or renal disease.

Entering the 2000s, it has been reported that proteins belonging to the BMP protein family (BMP2, BMP4, BMP6, BMP7, BMP9) have functions for adipose tissue differentiation in addition to bone formation functions. In particular, it has been reported that BMP8 or BMP9 has a function of increasing energy metabolism through promotion of brown adipogenesis and activation of brown adipose tissue. However, as a result of investigating the function of inducing bone differentiation for 14 types of BMP protein family in several studies and reviews, it was found that BMP2, BMP4, BMP6, BMP7, and BMP9 proteins markedly increased alkaline phosphatase activity, which is important for bone differentiation, and it was also been found that the proteins formed bone tissue in animal experiments. On the other hand, in these papers, BMP10 did not increase alkaline phosphatase activity, and bone tissue formation was not observed in animal experiments. These results suggest that several BMP proteins, except for BMP10, may promote brown adipogenesis, but may also promote bone differentiation at the same time, suggesting the possibility of acting as a side effect from the viewpoint of obesity and diabetes drug development. In fact, papers and patents on the development of bone-forming therapeutics using BMP2 or BMP7, and examples of commercialization development may be easily found, but obesity treatment using them has not been identified.

DISCLOSURE OF THE INVENTION

Technical Goals

An object of the present disclosure is to provide a composition containing bone morphogenetic protein 10 as an active ingredient as a composition for preventing or treating metabolic diseases such as obesity, diabetes, and dyslipidemia.

Technical Solutions

The present disclosure provides a pharmaceutical composition for preventing or treating metabolic diseases containing bone morphogenetic protein 10 (BMP10) as an active ingredient.

In addition, the present disclosure provides a health food for preventing or improving metabolic diseases containing bone morphogenetic protein 10 (BMP10) as an active ingredient.

Advantageous Effects

According to the present disclosure, it was found that brown adipogenesis was promoted in mouse embryonic mesenchymal cell line C3H10T1/T2 cells treated with bone morphogenetic protein 10 (BMP10), and that browning of stromal vascular fraction adipose stem cells isolated from subcutaneous adipose tissue was increased. Further, weight loss, improvement in insulin resistance, and changes in blood lipid concentrations were found in obese animal models induced by a high-fat diet. Accordingly, a composition containing BMP10 as an active ingredient may be provided as a preventive or therapeutic agent for metabolic diseases including obesity, diabetes and dyslipidemia.

BRIEF DESCRIPTION OF DRAWINGS

FIG. 4 shows a result of determining a browning effect of BMP10 on day 4 of differentiation induction after treating adipose stem cells of stromal vascular fraction (SVF) isolated from subcutaneous fat of mice with BMP10.

FIG. 5 shows Western blot results determining expression levels of brown adipose markers in cells on day 4 of differentiation induction after treating adipose stem cells of the stromal vascular fraction (SVF) isolated from subcutaneous fat of mice with BMP9 and BMP10.

FIG. 6 shows results of determining expression levels of BMP10 in the heart and blood of mice exercised for 4 weeks.

FIG. 7 shows results of determining a metabolic disease improvement effect of recombinant BMP10 in a high-fat diet-induced obesity model by administering recombinant BMP10 to mice fed a high-fat diet for 6 weeks (1.0 mg/kg, ip, qd) intraperitoneally once a week for 6 weeks to determine a weight change, diabetes improvement effect, and blood lipid change.

BEST MODE FOR CARRYING OUT THE INVENTION

Hereinafter, the present disclosure will be described in detail.

Bone morphogenetic protein 10 (BMP10) is a protein expressed in the heart and is known to play an important role in heart development in the developmental stage, and is known to have a rapid decrease in blood concentration after birth and to be hardly expressed in adulthood. The inventors completed the present disclosure by confirming that BMP10 exhibited a promoting effect on adipose tissue differentiation, particularly brown adipogenesis and browning of white adipose tissue.

The present disclosure can provide a pharmaceutical composition for preventing or treating metabolic diseases containing bone morphogenetic protein 10 (BMP10) as an active ingredient.

The bone morphogenetic protein 10 (BMP10) is NCBI Entrez Gene number 27302.

The bone morphogenetic protein 10 may induce brown adipocyte differentiation.

The bone morphogenetic protein 10 may induce browning of white adipose tissue.

In addition, the bone morphogenetic protein 10 may increase expression of browning marker Ucp1.

The metabolic disease may be selected from the group consisting of obesity, diabetes and dyslipidemia.

The brown fats are adipose tissue that is distinguished from white adipose tissue, which is generally stored fat, because they are brown in color. They are formed of cells rich in mitochondria and oil, and has many sympathetic nerve fibers, so they have excellent metabolic activities, especially lipolysis and fatty acid oxidation.

In addition, it has been reported that browning, in which white adipose tissue changes similarly to brown adipose tissue, increases energy expenditure. Exercise methods or drugs capable of inducing brown adipocyte differentiation and browning induce an increase in energy expenditure, drawing attention as a field of treatment for metabolic diseases such as obesity and diabetes.

Figure 2:
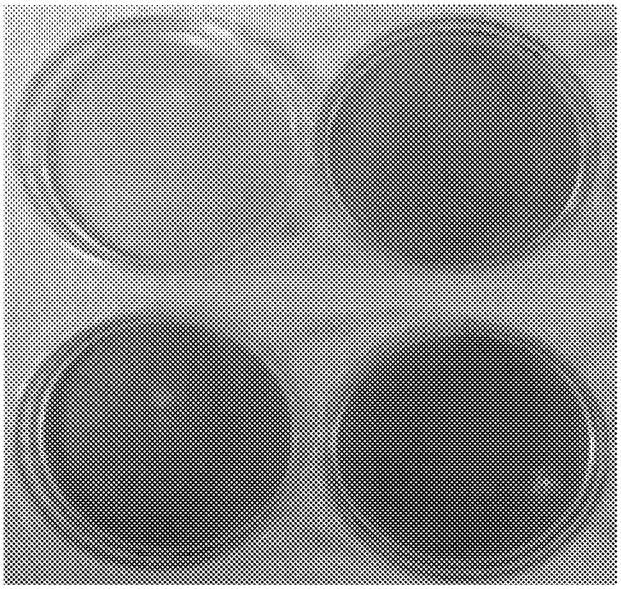
FIG. 2 shows results of determining a degree of brown adipocyte differentiation in C3H10T1/T2 cells, a mouse embryonic mesenchymal cell line in which adipocyte differentiation was induced, on days 4 and 8 of differentiation induction after treatment with BMP10.
Figure 3:
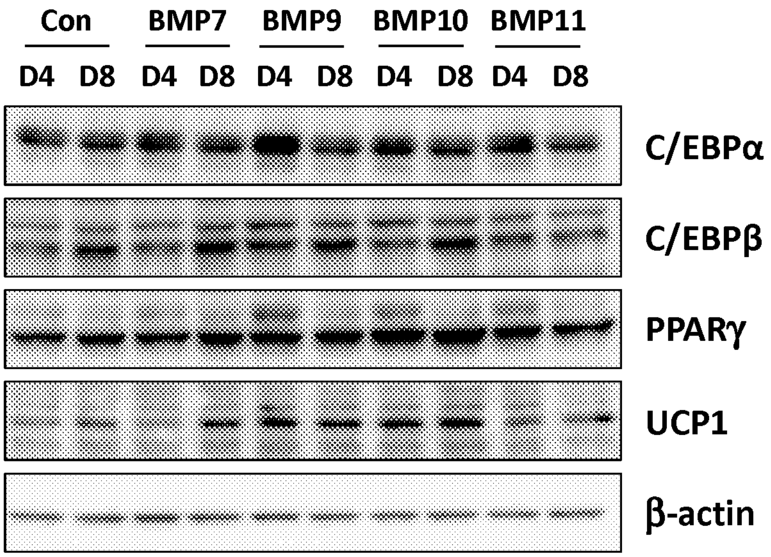
FIG. 3 shows results of Western blotting determining expression levels of brown fat markers in C3H10T1/T2 cells, a mouse embryonic mesenchymal cell line in which adipocyte differentiation was induced, on days 4 and 8 of differentiation induction after treatment with BMP7, BMP9, BMP10, and BMP11.

The present disclosure is a technology confirming that the brown adipocyte differentiation ability and browning of white adipose tissue are effectively induced by bone morphogenetic protein 10 (BMP10). According to an embodiment of the present disclosure, as a result of treating mouse embryonic mesenchymal stem cells induced to differentiate with adipocytes with BMP10 and determining a brown adipocytes differentiation ability, an increase in cells differentiated into brown adipocytes was confirmed from the 4th day after adipocytes differentiation was induced in the group of cells treated with BMP10 as shown in FIG. 2. In addition, as shown in FIG. 3, expression of Ucp1, a major marker of brown fat, was found to be greatly increased in BMP10-treated cells.

In addition, according to another embodiment of the present disclosure, as a result of determining the effect of BMP10 on inducing browning by isolating adipose stem cells of the stromal vascular fraction (SVF) from the subcutaneous fat of a mouse, and treating the isolated adipose stem cells with BMP10, as shown in FIG. 4, it was found that browning of the stromal vascular fraction-derived adipose stem cells treated with BMP10 was increased compared to a control group.

From the above results, the composition containing bone morphogenetic protein 10 (BMP10) as an active ingredient induces brown adipocyte differentiation and browning of white adipose tissue, which can be converted into brown adipose tissue with excellent lipolysis and fatty acid oxidation effects. Since effective fat reduction can be induced through this browning, the BMP10 may be provided as a composition for preventing or treating metabolic diseases.

The pharmaceutical composition may be included in an amount of 0.1 to 90 parts by weight based on 100 parts by weight of the total pharmaceutical composition.

In one example embodiment of the present disclosure, the pharmaceutical composition for preventing or treating metabolic diseases containing the bone morphogenetic protein 10 as an active ingredient may use any one formulation selected from the group consisting of injections, granules, powders, tablets, pills, capsules, suppositories, gels, suspension, emulsion, drop, or solution, in accordance with conventional methods.

In another example embodiment of the present disclosure, a pharmaceutical composition for preventing or treating obesity containing bone morphogenetic protein 10 as an active ingredient may further include at least one additive selected from the group consisting of a suitable carrier, excipient, disintegrant, sweetener, coating agent, swelling agent, a lubricant, a polishing agent, a flavoring agent, an antioxidant, a buffer, a bacteriostatic agent, a diluent, a dispersing agent, a surfactant, a binder, and a lubricant.

Specifically, as the carrier, excipient and diluent, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline Cellulose, polyvinyl pyrrolidone, water, methylhydroxybenzoate, propylhydroxybenzoate, talc, magnesium stearate, and mineral oil may be used, and solid preparations for oral administration include tablets, pills, powders, granules, and capsules. These solid preparations may be prepared by mixing at least one or more excipients, for example, starch, calcium carbonate, sucrose or lactose, gelatin, etc., with the composition. In addition to simple excipients, lubricants such as magnesium stearate and talc may also be used. Liquid preparations for oral administration include suspensions, solutions for oral use, emulsions, syrups, and the like, and various excipients such as wetting agents, sweeteners, aromatics, and preservatives may be included in addition to commonly used simple diluents such as water and liquid paraffin. Preparations for parenteral administration include sterilized aqueous solutions, non-aqueous solvents, suspensions, emulsions, freeze-dried preparations, suppositories, and the like. Propylene glycol, polyethylene glycol, vegetable oils such as olive oil, and injectable esters such as ethyl oleate may be used as non-aqueous solvents and suspending agents. As a base material of the suppository, witepsol, macrogol, tween 61, cacao butter, laurin fat, glycerogeratin and the like may be used.

According to one embodiment of the present disclosure, the pharmaceutical composition may be administered to a subject in a conventional manner via intravenous, intraarterial, intraperitoneal, intramuscular, intraarterial, intraperitoneal, intrasternal, transdermal, intranasal, inhalation, topical, rectal, oral, intraocular, or intradermal routes.

A preferred dosage of the bone morphogenetic protein 10 may vary depending on the condition and body weight of the subject, the type and extent of the disease, the drug form, the route and duration of administration, and may be appropriately selected by a person skilled in the art. According to one embodiment of the present disclosure, although not limited thereto, the daily dosage may be 0.01 to 200 mg/kg, specifically 0.1 to 200 mg/kg, and more specifically 0.1 to 100 mg/kg. Administration may be conducted once a day or in several divided doses, but the scope of the present disclosure is not limited thereby.

In the present disclosure, the term 'subject' may refer to a mammal including human, but is not limited to these examples.

The present disclosure can provide a health food for preventing or improving metabolic diseases containing bone morphogenetic protein 10 (BMP10) as an active ingredient.

The health food is used together with other foods or food additives in addition to the bone morphogenetic protein 10, and may be appropriately used according to a conventional method. The mixing amount of the active ingredient may be appropriately determined depending on the purpose of use thereof, for example, prevention, health or therapeutic treatment.

The effective dose of the compound contained in the health food may be used according to the effective dose of the therapeutic agent, but may be less than the above range in the case of long-term intake for the purpose of health and hygiene or health control. Since the active ingredient has no problem in terms of safety, it is clear that it may be used in quantities greater than the above range.

There is no particular limitation on the type of health food, and examples include meat, sausage, bread, chocolate, candy, snacks, confectionery, pizza, ramen, other noodles, gum, dairy products including ice cream, various soups, beverages, tea, drinks, alcoholic beverages, vitamin complexes, and the like.

MODES FOR CARRYING OUT THE INVENTION

Hereinafter, examples will be described in detail to aid understanding of the present disclosure. However, the following examples are merely illustrative of the present disclosure, but the scope of the present disclosure is not limited to the following examples. The embodiments of the present disclosure are provided to more completely explain the present disclosure to those skilled in the art.

<Example 1> Induction of Brown Adipogenesis by BMP Protein

Figure 1:
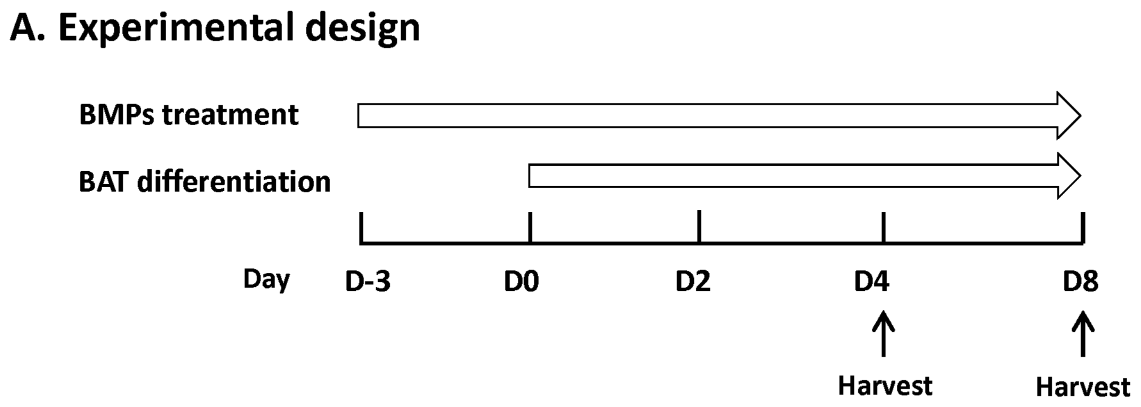
FIG. 1 is an experimental process performed to determine a brown adipocyte differentiation ability of bone morphogenetic protein 10 (BMP10).

In order to evaluate the brown adipogenesis ability of proteins belonging to the BMP group, including BMP10, the brown adipocyte differentiation ability was evaluated using C3H10T1/T2 cells, a mouse embryonic mesenchymal cell line, or stem cells of the stromal vascular fraction isolated from subcutaneous adipose tissue by the process shown in FIG. 1.

Treatment with BMP proteins started 3 days before induction of brown adipogenesis and continued until the end of the differentiation process. To induce brown adipogenesis, a cocktail for brown adipogenesis including 20 nM insulin, 1 nM T3, 5 μM dexamethasone, 0.5 mM isobutylmethylxantine, 0.125 μM indomethacin, and 1 μM rosiglitazone was treated for 8 days from day 0 (D0). The degree of differentiation and the expression of brown fat markers at each stage were identified by sampling on day 4 (D4) and day 8 (D8), respectively, after differentiation induction.

<Example 2> Confirmation of Promotion Effect of BMP10 on Brown Adipocyte Differentiation In order to determine the ability of BMP10 to induce differentiation into brown adipocytes, cells on day 4 and day 8 after differentiation was induced as in Example 1 were stained with Oil-Red O, and the state of differentiation into brown adipocytes was observed.

As a result, as shown in FIG. 2, it was confirmed that the cell group treated with BMP10 rapidly differentiated into brown adipocytes from day 4 of differentiation induction compared to the control group, and even at the final stage, on day 8, it was confirmed that brown adipogenesis was promoted in the cell group treated with BMP10 compared to the control group.

From the above results, it was confirmed that BMP10 promoted brown adipocyte differentiation from an early stage and exhibited the brown adipogenesis ability.

<Example 3> Confirmation of Induction of Expression of Adipocyte Differentiation Markers by BMP10

In order to further confirm the ability of BMP10 to promote brown adipogenesis confirmed in the previous experiment, changes in the expression of brown adipogenesis markers were confirmed by Western blotting.

In the same manner as in Example 1, all proteins of the cells on day 4 and day 8 after brown adipogenesis were induced were isolated, respectively, and changes in expression level were observed using antibodies for each marker.

As a result, it was confirmed that the expression of each marker was increased from day 4 in the BMP10-treated cells compared to the control group as shown in FIG. 3. In particular, it was confirmed that the expression of Ucp1, a major marker of brown fat, was increased only in the BMP10-treated cells.

From the above results, it was confirmed that BMP10 effectively induced differentiation into brown adipocytes.

<Example 4> Confirmation of Browning Effect of BMP10 in Stromal Vascular Fraction Isolated from Subcutaneous Adipose Tissue Recently, as it has been reported that browning, in which white adipose tissue changes similarly to brown adipose tissue during exercise or low temperature environment, increases energy expenditure, in order to confirm whether the ability of BMP10 to induce differentiation into brown adipocytes, which was confirmed in the previous experiment, could also be used in the field of metabolic disease treatment, adipose stem cells of the stromal vascular fraction (SVF) were isolated from the subcutaneous fat of mice and the effect of BMP10 of inducing browning was confirmed using the adipose stem cells.

Browning was induced by the same process as in FIG. 1. As the brown adipogenesis by BMP10 was increased from day 4 in the previous experiment, the browning of BMP10 was compared with the control group.

As a result, as shown in FIG. 4, it was confirmed that the browning of SVF-derived adipose stem cells on day 4 was promoted by BMP10 compared to the control group.

From the above results, it was confirmed that BMP10 not only promotes brown adipogenesis but also promotes browning of white adipocytes.

<Example 5> Confirmation of Browning Marker Expression Level by BMP10 in Stromal Vascular Fraction Isolated from Subcutaneous Adipose Tissue In order to further confirm the ability of BMP10 to induce browning confirmed in the previous experiment, the stromal vascular fraction isolated from subcutaneous adipose tissue was treated with BMP9 and BMP10, and the change in the expression level of the browning marker was observed by real-time quantitative PCR.

As a result, as shown in FIG. 5, it was confirmed that the expression of browning markers was significantly increased in the experimental group treated with BMP10 compared to the control group, and in particular, it was confirmed that the expression of Ucp1, the major marker of browning, was greatly increased in BMP10 than in BMP9.

From the above results, it was confirmed that the browning effect of BMP10 was superior to that of other BMP groups.

<Example 6> Confirmation of BMP10 Expression Level in Mice Exercised for 4 Weeks According to a recent report, it is known that browning of white adipose tissue is promoted by irisin secreted from muscles by exercise. Accordingly, it was determined whether the expression and secretion of BMP10 in the heart could be increased in an environment in which browning was promoted.

To this end, the changes in BMP10 expression in the heart and blood of 57Bl/6J mice (12 weeks old, male) subjected to an endurance test through treadmill exercise for 4 weeks were determined by performing real-time quantitative PCR and ELISA, respectively.

As a result, as shown in FIG. 6, the expression of BMP10 mRNA was increased in the heart tissue of the mice exercised for 4 weeks, and an increase in BMP10 protein was also confirmed in the blood of the mice.

From the above results, it was confirmed that BMP10, which increased in the blood during exercise, could be secreted into the blood to promote brown adipogenesis and browning.

<Example 7> Confirmation of Effect of Improving Metabolic Disease of Recombinant BMP10 in High-Fat Diet-Induced Obesity Model In order to confirm the effects of promoting brown adipogenesis and browning of white adipose tissue and increasing BMP10 in the heart and blood by exercise, which were confirmed in previous experiments, in improving metabolic diseases, a high-fat diet-induced obese mouse model was used to determine effects of improving obesity and diabetes.

Recombinant BMP10 was administered intraperitoneally (1.0 mg/kg, ip, qd) once a week for 6 weeks to mice fed a high-fat diet for 6 weeks, and body weight changes were observed.

As a result, as shown in FIG. 7, after administration of recombinant BMP10 for 6 weeks, a tendency to decrease in whole body fat mass was observed, and it was confirmed the increase in whole body fat mass compared to before administration was lower than that of the control group. However, no change in food intake compared to the control group was observed during the period of the recombinant BMP10 administration.

In addition, as a result of determining the diabetes improvement effect of BMP10, it was confirmed that fasting blood glucose was significantly lowered. In a glucose tolerance test, although there was no difference in glucose tolerance between the recombinant BMP10-administered group and the control group, it was confirmed that recombinant BMP10 has an ability of improving insulin resistance, because insulin secretion was significantly lower than that of the control group.

Finally, as a result of observing changes in blood lipids after administration for 6 weeks, blood triglycerides exhibited a decreasing trend, and total cholesterol was found to be significantly reduced.

From the above results, it was confirmed that BMP10 was effective in improving obesity, diabetes and dyslipidemia.

Having described specific parts of the present disclosure in detail above, it is clear to those skilled in the art that these specific descriptions are only preferred embodiments, and the scope of the present disclosure is not limited thereby. Accordingly, the substantial scope of the present disclosure will be defined by the appended claims and their equivalents.

The invention claimed is:

1. A method of reducing insulin resistance in a subject in need thereof, comprising:

parenterally administering a pharmaceutical composition comprising bone morphogenetic protein 10 (BMP10) as an active ingredient to the subject.

2. The method of claim 1, wherein the BMP10 is present in the pharmaceutical composition in an amount of 0.1 to 90 parts by weight per 100 parts by weight of the total pharmaceutical composition.

3. A method of reducing total blood cholesterol levels in a subject in need thereof, comprising:

parenterally administering a pharmaceutical composition comprising bone morphogenetic protein 10 (BMP10) as an active ingredient to the subject.

4. The method of claim 3, wherein the BMP10 is present in the pharmaceutical composition in an amount of 0.1 to 90 parts by weight per 100 parts by weight of the total pharmaceutical composition.

* * * * *